United States Patent
Umemoto

(10) Patent No.: US 10,238,552 B2
(45) Date of Patent: Mar. 26, 2019

(54) PERSONAL ABSORBENT ARTICLE HAVING THREE DIMENSIONAL GATHERS

(71) Applicant: DAIO PAPER CORPORATION, Shikokuchuo-shi, Ehime (JP)

(72) Inventor: Kaori Umemoto, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 760 days.

(21) Appl. No.: 14/402,279

(22) PCT Filed: May 28, 2013

(86) PCT No.: PCT/JP2013/064749
§ 371 (c)(1),
(2) Date: Nov. 19, 2014

(87) PCT Pub. No.: WO2013/180117
PCT Pub. Date: Dec. 5, 2013

(65) Prior Publication Data
US 2015/0216734 A1    Aug. 6, 2015

(30) Foreign Application Priority Data

May 28, 2012   (JP) ................. 2012-120703

(51) Int. Cl.
| | |
|---|---|
| A61F 13/15 | (2006.01) |
| A61F 13/20 | (2006.01) |
| A61F 13/475 | (2006.01) |
| A61F 13/472 | (2006.01) |
| A61F 13/494 | (2006.01) |

(52) U.S. Cl.
CPC .......... *A61F 13/4753* (2013.01); *A61F 13/15* (2013.01); *A61F 13/472* (2013.01); *A61F 13/494* (2013.01)

(58) Field of Classification Search
CPC ......................... A61F 13/4753; A61F 13/494
See application file for complete search history.

(56) References Cited

U.S. PATENT DOCUMENTS

2011/0077613 A1    3/2011  Kurihara

FOREIGN PATENT DOCUMENTS

| JP | 11-19120 | 1/1999 |
|---|---|---|
| JP | 11-104174 | 4/1999 |
| JP | 2002-45396 | 2/2002 |
| JP | 2006-175022 | 7/2006 |
| JP | 2009-285241 | 12/2009 |
| JP | 2012-81065 | 4/2012 |

*Primary Examiner* — Michele M Kidwell
(74) *Attorney, Agent, or Firm* — Norris McLaughlin, P.A.

(57) ABSTRACT

A middle part in the width direction of a three-dimensional gather of an absorbent article is joined with a side edge portion of a liquid permeable surface sheet, and a folded portion folded back to a side at an inner side of the joint portion is formed. The folded portion is defined by an end area, a urinary-opening facing area, and a middle area. In the end area and the middle area, a portion on an inner side in the width direction of the folded portion is joined with the liquid permeable surface sheet, and a projection with an end of a portion on an outer side in the width direction rather than the joint portion as a free end portion is formed.

3 Claims, 8 Drawing Sheets

[Fig. 1]
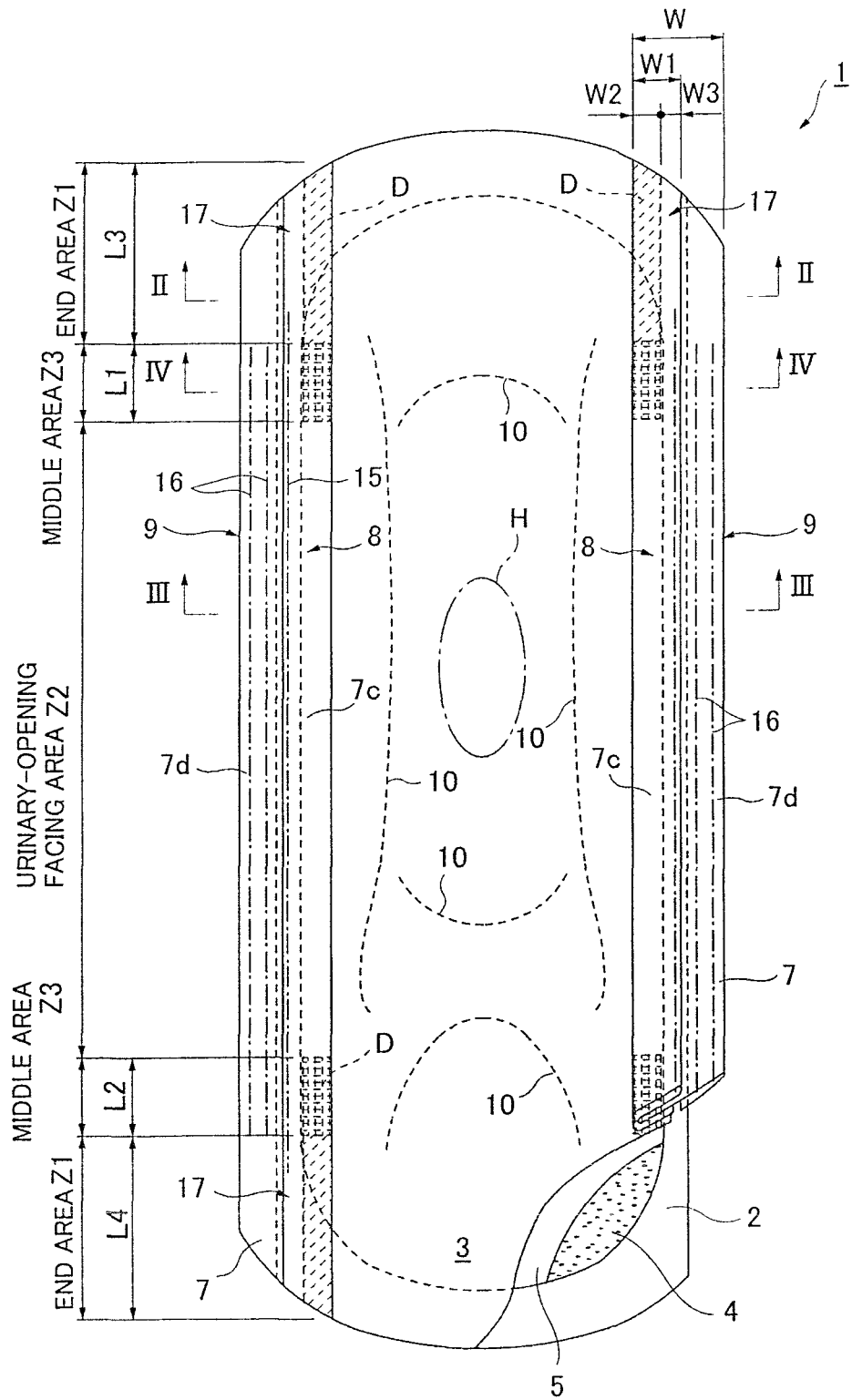

[Fig. 2]
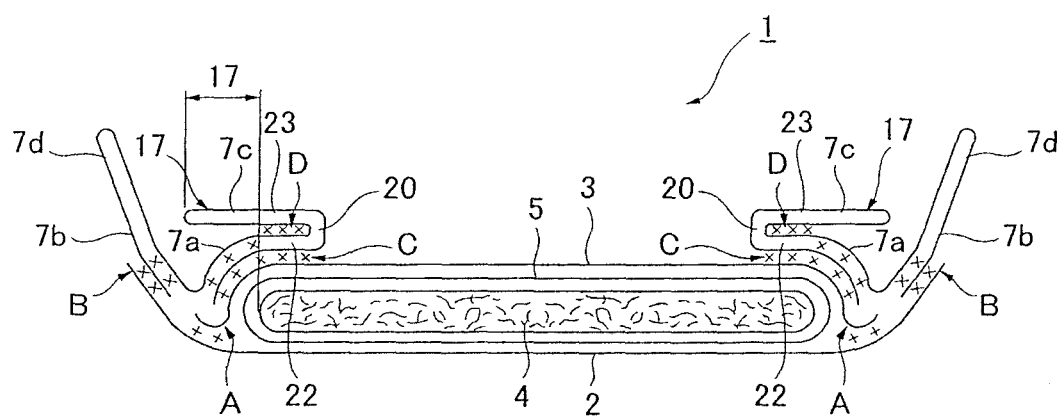
[Fig. 3]
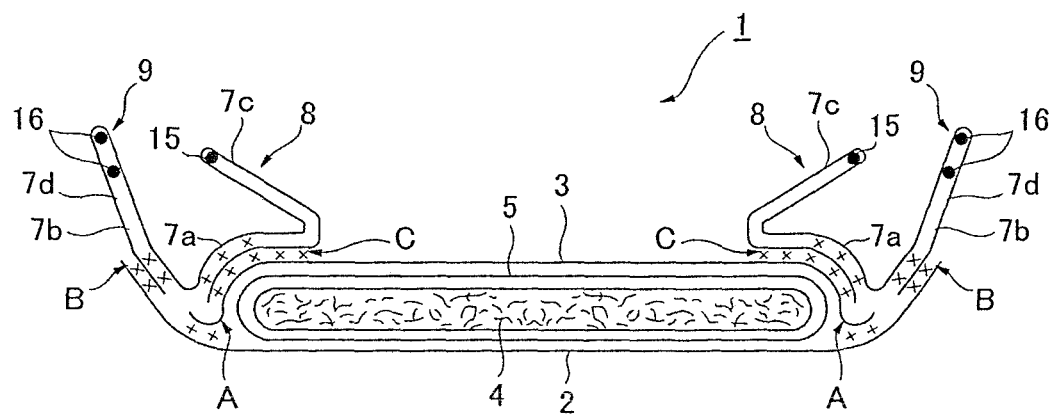

【Fig. 4】
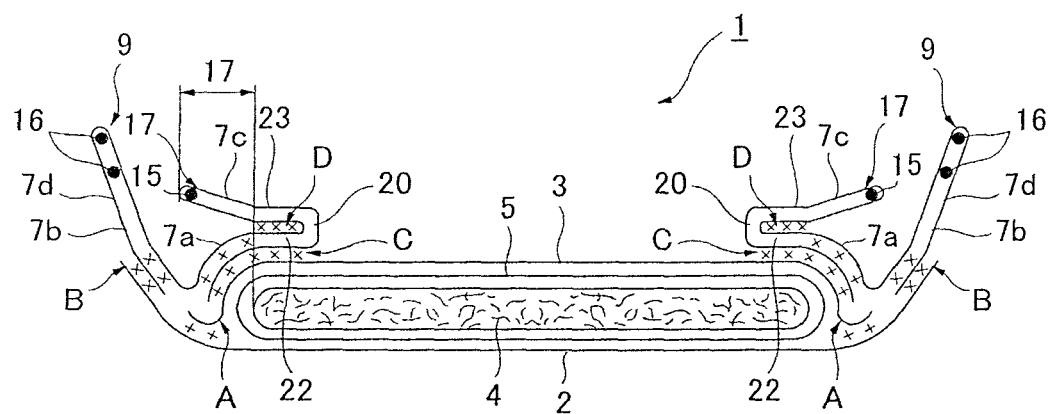
【Fig. 5】
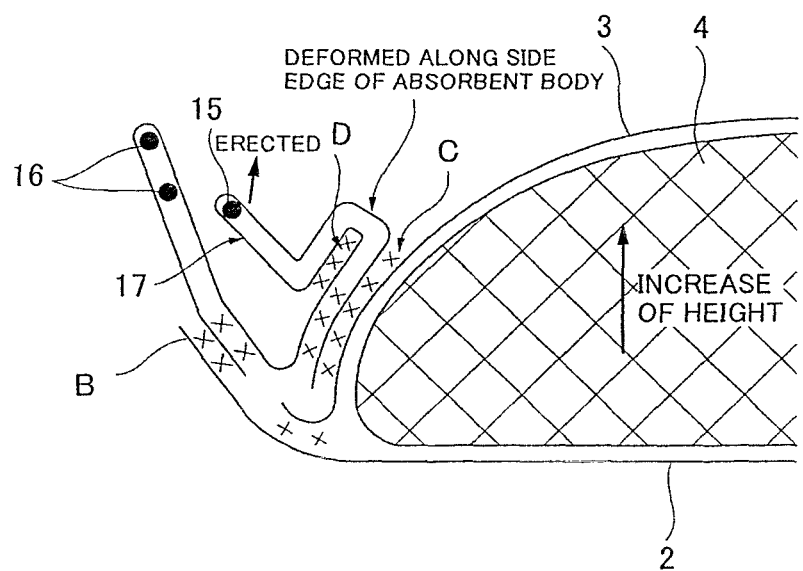

[Fig. 6]
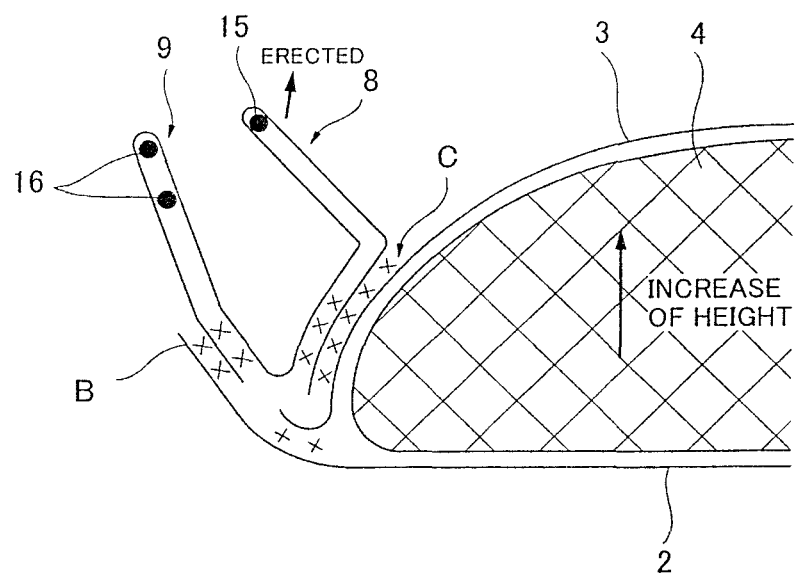
[Fig. 7]
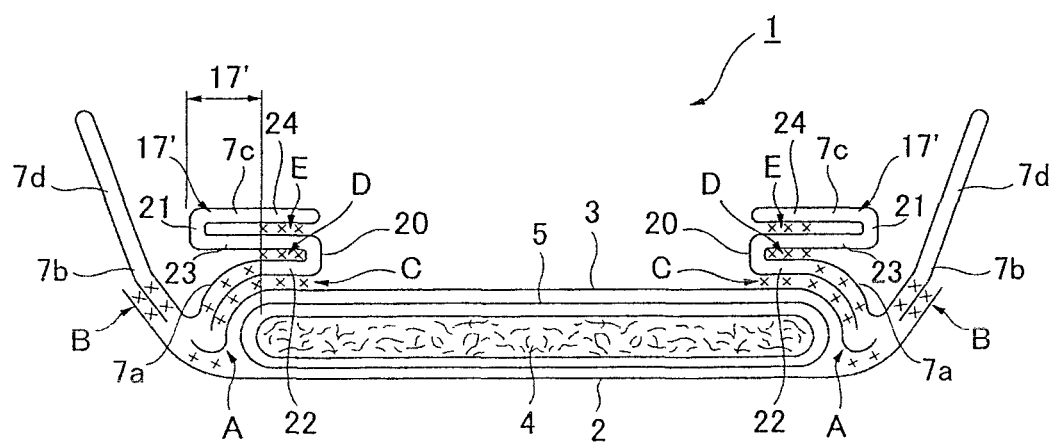

[Fig. 8]
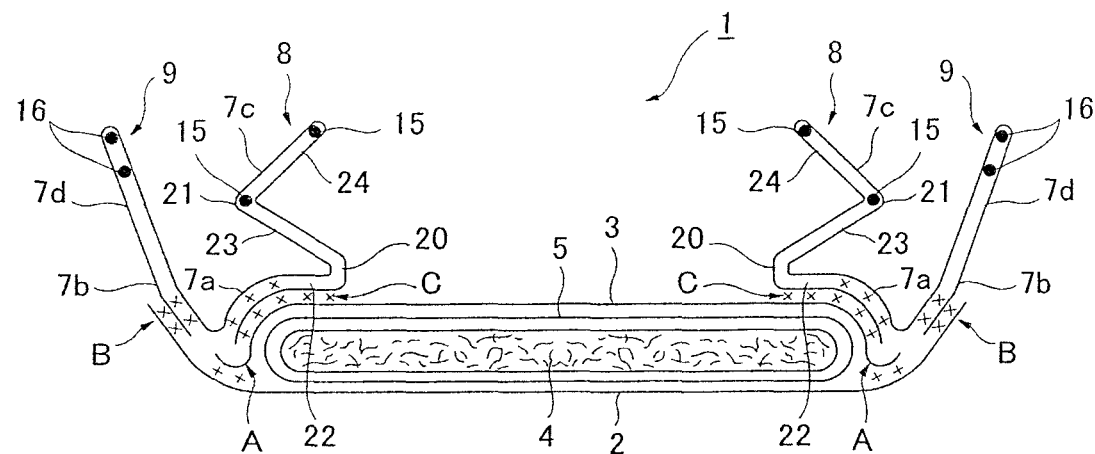
[Fig. 9]
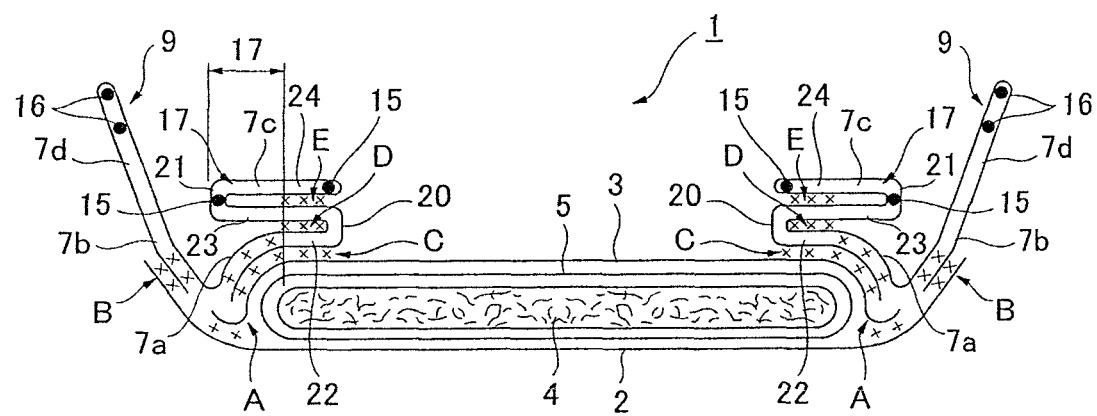

[Fig. 10]
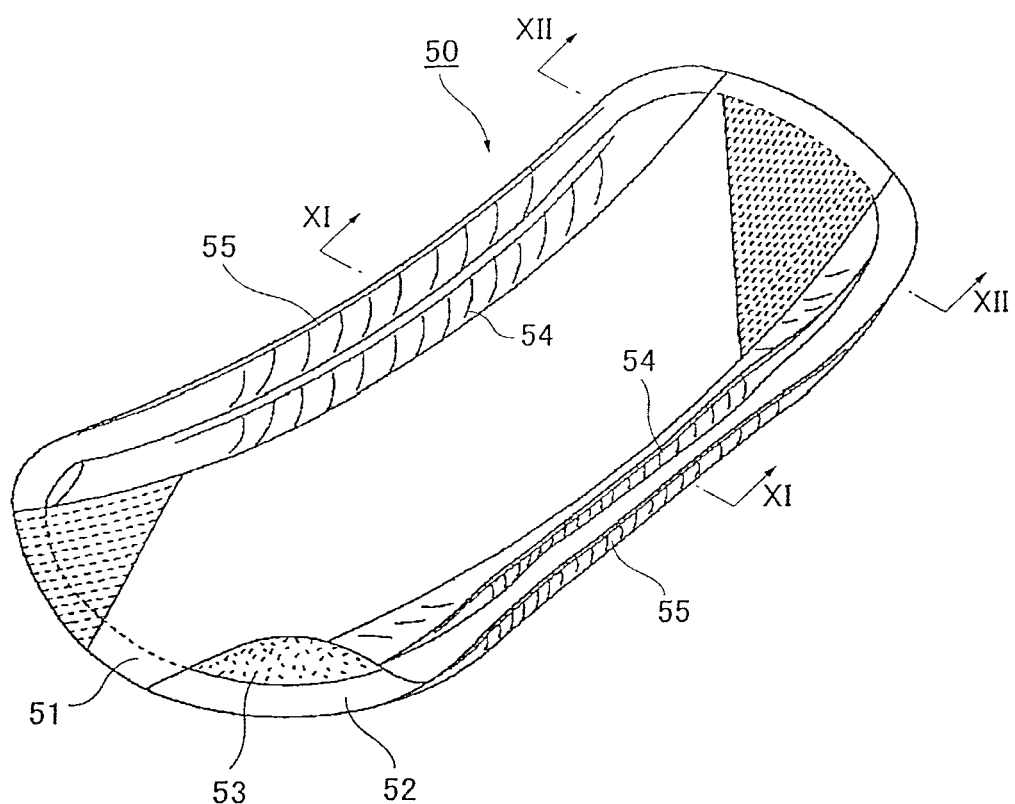
RELATED ART

[Fig. 11]
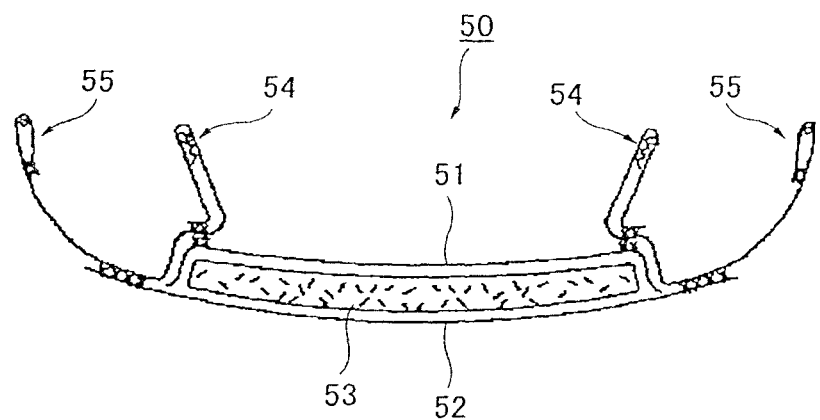
RELATED ART
[Fig. 12]
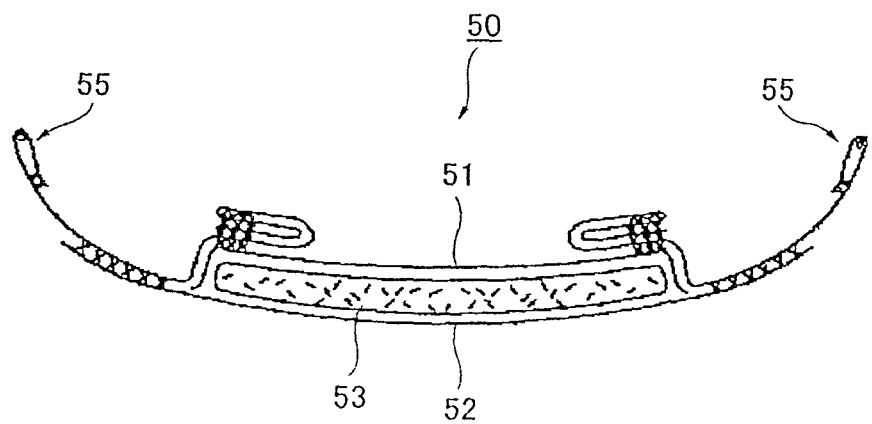
RELATED ART

[Fig. 13]
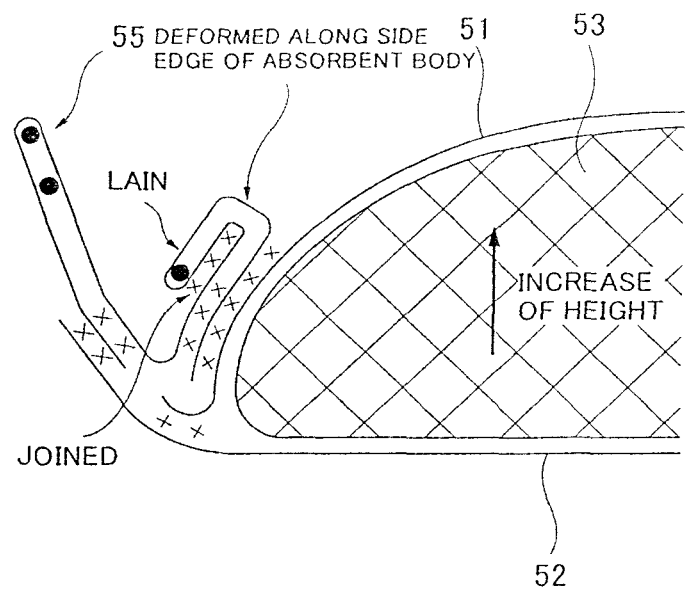
RELATED ART
[Fig. 14]
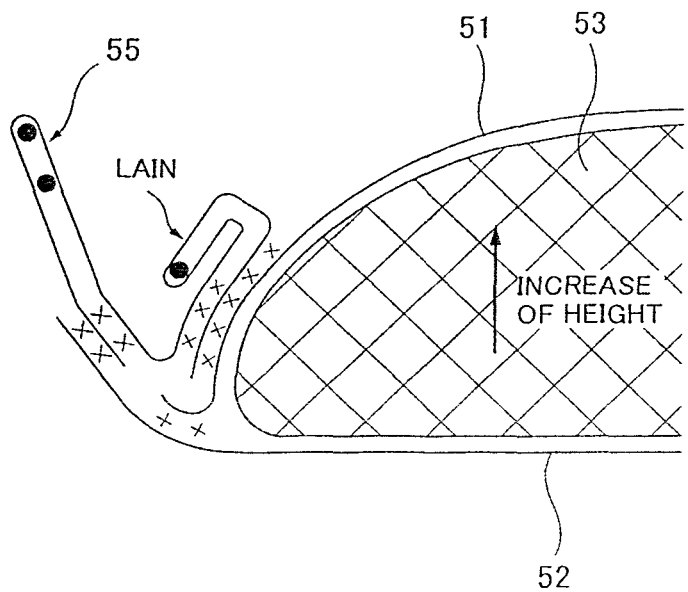
RELATED ART

PERSONAL ABSORBENT ARTICLE HAVING THREE DIMENSIONAL GATHERS

BACKGROUND OF THE INVENTION

The present invention relates to an absorbent article such as a sanitary napkin, a panty liner, and an incontinence pad for absorbing menstrual blood, vaginal discharge, and urine, for example, and more particularly to an absorbent article having a pair of right and left three-dimensional gathers erect on a skin side by gather-forming nonwoven fabric arranged at both sides of a liquid permeable surface sheet along the longitudinal direction.

Conventionally, there is known, as an absorbent article such as a sanitary napkin, a panty liner, a vaginal discharge sheet, and an incontinence pad, an absorbent article in which an absorbent body composed of cotton-like pulp and the like is interposed between a liquid impermeable back surface sheet composed of a polyethylene sheet or polyethylene laminate nonwoven fabric, for example, and a liquid permeable surface sheet composed of nonwoven fabric or a porous plastic sheet, for example.

Such a kind of absorbent article has been improved various times, and an absorbent article having double three-dimensional gathers is proposed, as illustrated in FIG. 10 to FIG. 12. As disclosed in Japanese Patent Application Laid-open No. H11-19120, an absorbent article 50 having such double three-dimensional gathers is the absorbent article 50 having an absorbent body 53 interposed between a liquid permeable surface sheet 51 and a liquid impermeable back surface sheet 52, includes, at each of both sides of the absorbent article 50, a first three-dimensional gather 54 formed to project on a skin side with a position near the substantially side edge of the absorbent body 53 as an erection base end and a second three-dimensional gather 55 formed at a relatively outer position of the first three-dimensional gather 54 and formed to project on a skin side by nonwoven fabric arranged to be substantially continuous from the surface of the liquid impermeable back surface sheet 52.

The absorbent article having such double three-dimensional gathers completely prevents side leakage of body fluids such as menstrual blood and vaginal discharge, and exerts the effect of preventing dirt of panties.

Moreover, the above-described absorbent article having double three-dimensional gathers has been also improved various times, and Japanese Patent Application Laid-open No. 2006-175022 proposes an absorbent article effectively preventing side leakage, etc. when used, by joining a side flap (corresponding to the second three-dimensional gather 55) and a three-dimensional cuff (corresponding to the first three-dimensional gather 54) at each of both ends in the longitudinal direction of the absorbent article or the vicinity of each of the both ends so as to secure the erection property of the side flap and the three-dimensional cuff.

Moreover, Japanese Patent Application Laid-open No. H11-104174 proposes an absorbent article in which a thread-like elastic member is disposed at a region near the erection base end of the second three-dimensional gather portion along a substantially longitudinal direction of the absorbent article, and a thread-like elastic member is disposed at each erection end region, whereby the thread-like elastic member disposed at the region near the erection base end acts for effectively erecting the side portion of the liquid impermeable back surface sheet, so that the base end portion of the second three-dimensional gather is erected upward by the thread-like elastic member, and the gather end portion is fit along a leg securely and flexibly by the thread-like elastic member at the end side.

Moreover, Japanese Patent Application Laid-open No. 2002-45396 supposes an absorbent article in which the first three-dimensional gather is formed to project in an inward direction with a side upper surface position of the absorbent body as an erection base point, and the second three-dimensional gather is formed to project in an outward direction substantially with an upper surface position of the liquid impermeable back surface sheet as an erection base point, so that when attached, large-width space having a substantially V-shaped cross section, that is, space for retaining menstrual blood, for example, is securely formed by the first three-dimensional gather and the second three-dimensional gather, and the space state is maintained steadily.

SUMMARY OF THE INVENTION

However, in the recent incontinence pad, the absorbent body contains a high absorbent polymer to absorb and retain a large amount of urine, and thus when a large amount of urine is absorbed by such a high absorbent polymer, the volume of the absorbent body is increased and the height of the absorbent body is increased, which causes a problem of making it difficult to erect particularly the first three-dimensional gather 54 with side edge portion of the absorbent body as an erection end base.

To be more specific in the aspect, in the conventional absorbent article 50 before use, the center portion in the longitudinal direction of the first three-dimensional gather 54 is erected on a skin side with a position near a substantially side edge of the absorbent body 53 as an erection base end, as illustrated in FIG. 11, while the end portion in the longitudinal direction of the first three-dimensional gather 54 is folded with a point of approximately ½ of the height of an erected piece as a folded line and the joined face is attached on the absorbent body 53 by hot melt, for example, as illustrated in FIG. 12.

In such an absorbent article 50, when the height of the absorbent body 53 is increased by absorbing a large amount of urine, the first three-dimensional gather 54 is deformed, at the both end portions in the longitudinal direction, so that the three-dimensional gather erection end portion is inclined in a non-erection direction along the side edge of the absorbent body 53 expanded in the height direction, as illustrated in FIG. 13. Thus, also at the center portion in the longitudinal direction, the three-dimensional gather erection end portion is influenced by deformation of such both end portions and deformed to be inclined in a non-erection direction, as illustrated in FIG. 14. As a result, the first three-dimensional gather 54 lies on the side of the absorbent body 53, and the function of the first three-dimensional gather 54 as a barrier is lost, thus easily causing side leakage when urine is discharged continuously.

Then, the main object of the invention is to provide an absorbent article having three dimensional gathers erect on a skin side with a position near a substantially side edge of the absorbent body as an erection base end, that is capable of maintaining an erection state on a skin side even when a large amount of body fluids is absorbed by the absorbent body and preventing side leakage of the body fluids.

Solution to Problem

In order to solve the above problem, there is provided, as a first aspect of the invention, an absorbent article including an absorbent body interposed between a liquid permeable surface sheet and a back surface sheet, and a three-dimensional gather erect on a skin side by gather-forming nonwoven fabric arranged at each of both side portions of the liquid permeable surface sheet along a longitudinal direction, in which in the liquid permeable surface sheet, a middle part in a width direction is joined with a side edge portion of, a folded portion folded back to a side at an inner side of the joint portion is formed, and the folded portion is defined by an end area at both ends in the longitudinal direction of the absorbent article, a urinary-opening facing area including a region corresponding to a urinary opening and forming the three-dimensional gather, and a middle area between the end area and the urinary-opening facing area, in the end area and the middle area, a portion on an inner side in the width direction of the folded portion is joined with the liquid permeable surface sheet, and a portion on an outer side in the width direction rather than the joint portion constitutes a projection with an end as a free end portion, and in the urinary-opening facing area and the middle area, an elastic stretching member is arranged continuously at least in a region corresponding to the projection, along the longitudinal direction of the absorbent article.

In the aforementioned first aspect of the invention, in the end area and the middle area of the gather-forming nonwoven fabric, a portion on an inner side in the width direction of the folded portion is joined with the liquid permeable surface sheet, and a portion on an outer side in the width direction rather than the joint portion constitutes a projection with an end as a free end portion, while in the urinary-opening facing area and the middle area of the gather-forming nonwoven fabric, an elastic stretching member is arranged continuously at least in a region corresponding to the projection, along the longitudinal direction of the absorbent article. Therefore, even when a large amount of urine is absorbed by the absorbent body and the height of the absorbent body is increased, the projection is constantly erected on a skin side without being influenced by the state of deformation of the joint portion to the side of the liquid permeable surface sheet in the middle area, and the force pulling the end portion of the three-dimensional gather in the urinary-opening facing area in a non-erection direction is significantly reduced. As a result, the erection of the three-dimensional gather in the urinary-opening facing area can be maintained. Therefore, even when urine is discharged continuously, the function of the three-dimensional gather as a barrier is not lost, and the side leakage can be prevented securely.

There is provided, as a second aspect of the invention, the absorbent article according to the primary aspect of the invention, further including, on a relatively outer side of the three-dimensional gather, a second three-dimensional gather erect on a skin side by nonwoven fabric arranged to be substantially continuous from a surface of the back surface sheet.

In the invention according to the second aspect of the invention, it is possible, with the double three-dimensional gather, to maintain the erection state on a skin side more securely and prevent side leakage of body fluids.

There is provided, as a third aspect of the invention, the absorbent article according to the first or second aspect of the invention, in which the three-dimensional gather is a single gather obtained by folding back the gather-forming nonwoven fabric to a side at an inner side position of the absorbent body.

There is provided, as the invention according to a fourth aspect of the invention, the absorbent article according to the first or second aspect of the invention, in which the three-dimensional gather is a double gather obtained by folding back the gather-forming nonwoven fabric to a side at an inner side position of the absorbent body and folding back the gather-forming nonwoven fabric to an inner side at a side position of the absorbent body.

The invention according to the third and fourth aspects of the invention defines that the three-dimensional gather may be a single gather, a double gather, or a multiple gather with more than double stages.

As described above in detail, according to the invention, the absorbent article having three dimensional gathers erect on a skin side with a position near substantially side edge of the absorbent body as an erection base end, can maintain an erection state on a skin side even when a large amount of body fluids is absorbed by the absorbent body and prevent side leakage of the body fluids.

BRIEF DESCRIPTION OF THE DRAWINGS

FIG. 1 is a partially broken developed view of an incontinence pad 1 according to the invention.

FIG. 2 is a diagram viewed from the arrow direction of a II-II line of FIG. 1 (a cross section of an end area 21).

FIG. 3 is a diagram viewed from the arrow direction of a III-III line of FIG. 1 (a cross section of an urinary-opening facing area Z2).

FIG. 4 is a diagram viewed from the arrow direction of a IV-IV line of FIG. 1 (a cross section of a middle area Z3).

FIG. 5 is a cross section of the middle area Z3 when urine is absorbed by an absorbent body 4.

FIG. 6 is a cross section of the urinary-opening facing area Z2 when urine is absorbed by the absorbent body 4.

FIG. 7 is a diagram illustrating another embodiment of a first three-dimensional gather 8 viewed from the arrow direction of the II-II line of FIG. 1.

FIG. 8 is a diagram illustrating another embodiment of the first three-dimensional gather 8 viewed from the arrow direction of the III-III line of FIG. 1.

FIG. 9 is a diagram illustrating another embodiment of the first three-dimensional gather 8 viewed from the arrow direction of the IV-IV line of FIG. 1.

FIG. 10 is a perspective view of the conventional absorbent article 50.

FIG. 11 is a diagram viewed from the arrow direction of an XI-XI line of FIG. 10.

FIG. 12 is a diagram viewed from the arrow direction of a XII-XII line of FIG. 10.

FIG. 13 is a cross section of an end area when urine is absorbed by the absorbent body 53 of the conventional absorbent article 50.

FIG. 14 is a cross section of a center area when urine is absorbed by the absorbent body 53 of the conventional absorbent article 50.

DETAILED DESCRIPTION OF THE INVENTION

In the following, embodiments of the invention will be described in detail with reference to the enclosed drawings.

First Embodiment

As illustrated in FIG. 1 to FIG. 4, the incontinence pad 1 according to the invention includes a liquid impermeable back surface sheet 2 composed of a polyethylene sheet and a polypropen sheet, for example, a liquid permeable surface sheet 3 allowing urine, menstrual blood, vaginal discharge, etc. (hereinafter, correctively referred to as body fluids) to pass therethrough quickly, the absorbent body 4 interposed between the both sheets 2, 3 and composed of cotton-like pulp or synthetic pulp, for example, crepe paper 5 surrounding the absorbent body 4 for keeping the shape of the absorbent body 4 and improving diffusibility thereof, and gather-forming nonwoven fabric 7, 7 arranged at both sides of the surface along a longitudinal direction. The gather-forming nonwoven fabric 7, 7 constitutes a pair of right and left three-dimensional gathers 8, 8 arranged to be erect on a skin side with a position near a substantially side edge of the absorbent body 4 as an erection base end, and a pair of right and left three-dimensional gathers 9, 9 that are arranged on the relatively outer side of the first three-dimensional gathers 8 and formed to be erect on a skin side by nonwoven fabric substantially extended from the surface of the liquid impermeable back surface sheet 2.

The following will further describe the structure of the incontinence pad 1 in detail.

As the liquid impermeable back surface sheet 2, there is used a sheet material having at least water imperviousness, such as an olefin resin sheet such as polyethylene and polypropylene. In addition, there can be used laminate nonwoven fabric in which nonwoven fabric is laminated on a polyethylene sheet, etc., and a nonwoven fabric sheet while the impermeability is substantially secured by a waterproof film (in this case, the waterproof film and the nonwoven fabric constitute the liquid impermeable back surface sheet), for example. Recently, the liquid impermeable back surface sheet having moisture permeability has tended to be used in terms of stuffiness prevention. Such an impervious and moisture permeable sheet material is a microporous sheet obtained by melt kneading inorganic filler in olefin resin such as polyethylene and polypropylene to form a sheet and extending the sheet uniaxially or biaxially.

Next, porous or nonporous nonwoven fabric is preferably used as the liquid permeable surface sheet 3. As the material fiber constituting nonwoven fabric, there can be used, for example, synthetic fiber such as olefin such as polyethylene or polypropylene, polyester, and polyamide synthetic fiber, regenerated fiber such as rayon and cupra, and natural fiber such as cotton. Then, it is possible to use nonwoven fabric obtained by an appropriate processing method such as a spun lace method, a spun bond method, a thermal bond method, a melt-blown method, and a needle punching method. Among these processing methods, the spun lace method is excellent in flexibility, the spun bond method is excellent in drape, and the thermal bond method and the air-through method are excellent in bulkiness and softness.

The absorbent body 4 interposed between the liquid impermeable back surface sheet 2 and the liquid permeable surface sheet 3 is composed of fluff pulp and a high absorbent polymer, for example. The high absorbent polymer is mixed in the pulp constituting the absorbent body, as granular powder, for example. The above-described pulp includes chemical pulp obtained from wood, pulp formed of cellulose fiber such as dissolving pulp, and pulp formed of artificial cellulose fiber such as rayon and acetate. The coniferous tree pulp having larger fiber is used more preferably than the broad leaf tree pulp in terms of functions and price. It is desirable that the weight per unit area of the absorbent body 4 is 200 to 1000 g/m$^2$ and preferably 290 to 900 g/m$^2$ for the pulp, and 10 to 500 g/m$^2$ and preferably 15 to 400 g/m$^2$ for the high absorbent polymer.

Moreover, synthetic fiber may be mixed in the absorbent body 4. As the synthetic fiber, there can be used polyolefin such as polyethylene or polypropylene, polyester such as polyethylene terephthalate and polybutylene terephthalate, polyamide such as nylon, and a copolymer including them, for example. A mixture of two of them may be also used. Moreover, it is also possible to use conjugated fiber such as sheath-core type fiber with fiber having a high melting point as a core and fiber having a low melting point as a sheath, side-by-side fiber, and splittable fiber, for example. Regarding the synthetic fiber, when it is hydrophobic fiber, it is desirable to use synthetic fiber on which surface processing has been performed with a hydrophilizing agent so that the synthetic fiber has affinity relative to body fluids.

As in the embodiment, when the crape paper 5 surrounding the absorbent body 4 is provided, the crepe paper 5 is consequently interposed between the liquid permeable surface sheet 3 and the absorbent body 4, so that the body fluids are quickly diffused by the crepe paper 5 excellent in absorbability and the reverse of such body fluids is prevented.

At the laminated portion of the liquid permeable surface sheet 3 and the absorbent body 4, fit embosses 10 can be arranged, in an area including at least an urinary-opening portion H, with an appropriate pattern from the surface side of the liquid permeable surface sheet 3.

In the example illustrated in the drawings, the width size of the liquid permeable surface sheet 3 is slightly larger than the width of the absorbent body 4 and limited to cover the absorbent body 4, as illustrated in the center cross section of FIG. 3. The first three-dimensional gathers 8 and the second three-dimensional gathers 9 formed on the outer side of the first three-dimensional gathers 8 are composed of the gather-forming nonwoven fabric 7 different from the liquid permeable surface sheet 3. As such gather-forming nonwoven fabric 7, there can be used nonwoven fabric having a structure of SSMS, SMS, SMMS, and so forth (wherein "S" denotes a spunbond layer and "M" denotes a meltblown layer), with synthetic fabric or regenerated fabric, as the material. In order to remove stiffness and prevent stuffiness, it is preferable to use nonwoven fabric having air permeability with a less basis weight. To be more specific, it is desirable to use nonwoven fabric formed with a basis weight of 5 to 25 g/m$^2$, and preferably 10 to 20 g/m$^2$. In addition, there is preferably used water repellent treated nonwoven fabric coated with a silicon-, paraffin metal-, or alkylchromic chloride-water repellent agent, for example, in terms of emphasis on functions of preventing body fluids from passing through or improving a texture, for example.

The structure of the first and second three-dimensional gathers 8, 9 will be described in more detail. Regarding the gather-forming nonwoven fabric 7, the both side portions in the width direction are folded back to the back surface side of the pad, whereby double sheet portions 7a, 7b are formed on the inner side in the width direction and on the outer side in the width direction, respectively. The double sheet portion 7a on the inner side in the width direction is adhered, at an end edge portion A on the liquid permeable surface sheet 3 corresponding to a side portion on the absorbent body 4, on the pad body by an adhesive agent such as a hot-melt adhesive agent. In addition, the double sheet portion 7b on the outer side in the width direction is adhered, at an end edge portion B on the liquid impermeable back surface sheet 2, on the pad body by an adhesive agent such as a hot-melt adhesive agent. Then, the part extended inward rather than an adhesive portion C of the double sheet portion 7a on the inner side in the width direction and the pad body is regarded as a folded portion 7c folded back outward in the width direction. The folded portion 7c constitutes the first three-dimensional gather 8, and an outward extending portion 7d extended outward rather than the end edge portion B of the liquid impermeable back surface sheet 2 constitutes the second three-dimensional gather 9. In the double sheets of the folded portion 7c and the outward extending portion 7d, elastic stretching members 15, 16 whose both ends and positions in the longitudinal direction are appropriately fixed are arranged at appropriate positions, respectively. The folded portion 7c and the outward extending portion 7d are erected on a skin side by contraction action of the elastic stretching members 15, 16, whereby the first three-dimensional gather 8 and the second three-dimensional gather 9 are formed, respectively. As the elastic stretching members 15, 16, yarn-like elastic stretching members are preferably used. It is desirable that the thickness is 300 to 100 dtex, and preferably 400 to 550 dtex.

The folded portion 7c extended inward rather than the adhesive portion C will be described in more detail. The folded portion 7c is defined, in the pad longitudinal direction, by the end area Z1 at both ends in the pad longitudinal direction, the urinary-opening facing area Z2 including a region corresponding to the urinary-opening portion H and forming the first three-dimensional gather 8, and the middle area Z3 between the end area Z1 and the urinary-opening facing area Z2, as illustrated in FIG. 1.

In the end area Z1 and the middle area Z3, as illustrated in FIG. 2 and FIG. 4, the base end side of the folded portion 7c is adhered, at an adhesive portion D, on the side of the liquid permeable surface sheet 3, that is, the surface side of the gather-forming nonwoven fabric 7 adhered at the adhesive portion C, by an adhesive agent such as a hot-melt adhesive agent, and a projection 17 is formed with the outer side in the width direction rather than the adhesive portion D as a free end portion.

In the incontinence pad 1 according to the first embodiment, the first three-dimensional gather 8 is a single gather obtained by folding back the gather-forming nonwoven fabric 7 to the side at a position on the inner side of the absorbent body 4, as illustrated in FIG. 3. To be more specific, in the end area Z1 and the middle area Z3, the gather-forming nonwoven fabric 7 adhered, at the adhesive portion C, on the side of the liquid permeable surface sheet 3 is folded in two by formation of a first folded portion 20 folded to the side at the inner side portion. The gather-forming nonwoven fabric 7 has a first folded surface 22 and a second folded surface 23, in the order from the lower layer side, and the second folded surface 23 is adhered on the first folded surface 22 at the adhesive portion D formed at a position closer to the first folded portion 20. Then, the first projection 17 is formed by a portion, in the second folded surface 23, on the outer side in the width direction rather than the adhesive portion D.

The adhesive portion D is preferably formed only in an area overlapping the absorbent body in plan view. In this manner, when a large amount of body fluids is absorbed and the height of the absorbent body 4 is increased, it is possible to suppress the projection 17 pulled to a non-erection direction of the first three-dimensional gather 8, and maintain erection of the first three-dimensional gather 8, as described later.

Moreover, in the urinary-opening facing area Z2 and the middle area Z3, as illustrated in FIG. 3 and FIG. 4, the elastic stretching member 15 is arranged continuously at least in a region corresponding to the projection 17, along the pad longitudinal direction. It is desirable that the elastic stretching member 15 is arranged at a position 1 mm or more inside from the end of the projection 17 so as to prevent a hard texture on a skin, and is arranged in a range of the projection 17 (a range on the outer side than the adhesive portion D). Thus, in the urinary-opening facing area Z2, the first three-dimensional gather 8 in which the entire folded portion 7c is erected on a skin side is formed, and in the middle area Z3, the projection 17 is erected on a skin side. Note that the elastic stretching member 15 is continuously arranged in the urinary-opening facing area Z2 and the middle area Z3, and in the end areas Z1, 21 on the both end sides in the longitudinal direction rather than such areas Z2, Z3, the elastic stretching member 15 is not arranged or is treated with discontinuity processing by cutting it finely.

In this manner, in the incontinence pad 1, as illustrated in FIG. 5, when a large amount of urine is absorbed by the absorbent body 4 and the height of the absorbent body 4 is increased in the middle area Z3, a portion joined with the side of the liquid permeable surface sheet 3 at the joint portion C and a portion where the gather-forming nonwoven fabric 7 is joined with each other at the joint portion D, in the gather-forming nonwoven fabric 7, are deformed so that the inner side projects on a skin side along the side edge of the absorbent body 4. However, the projection 17 is not influenced by such deformation states, and the free end portion is erected in an erection direction of the three-dimensional gather, similarly to the state before the body fluids are absorbed (see FIG. 4). Therefore, in the urinary-opening facing area Z2, as illustrated in FIG. 6, even when a large amount of urine is absorbed by the absorbent body 4 and the height of the absorbent body 4 is increased, it is possible to maintain the state of erection on a skin side and thus prevent side leakage of body fluids.

Moreover, the middle area Z3 in which the projection 17 is erected on a skin side is arranged between the urinary-opening facing area Z2 in which the first three-dimensional gather 8 is formed and the end area Z1 adhered on the side of the liquid permeable surface sheet 3. Thus, the erection height of the three-dimensional gather on a skin side decreases gradually from the center portion to the both end portions in the pad longitudinal direction. Therefore, it is possible to improve fitting feel to a skin and securely prevent side leakage of body fluids.

Meanwhile, at the outward extending portion 7d, the elastic stretching member 16 is arranged in a range almost same as the longitudinal direction range of the elastic stretching member 15 arranged at the folded portion 7c, and the range in which the elastic stretching members 16 is arranged is regarded as the second three-dimensional gather erect on a skin side. Note that on the both end portions in the longitudinal direction rather than such a range, the elastic stretching member is not arranged or is treated with discontinuity processing by cutting it finely.

At least one elastic stretching member 16 disposed in the second three-dimensional gather 9 may be arranged at a portion extended outward than the end edge portion B of the liquid impermeable back surface sheet 2, and two or more elastic stretching members 16 may be arranged with space from one another in the pad width direction, as illustrated in the example of the drawing. When two or more elastic stretching members are arranged, it is preferable to set an interval in the pad width direction to be equal to or smaller than 5 mm so as to prevent deterioration of the function as a barrier.

As illustrated in FIG. 1, it is desirable that the length W1 along the width direction of the member of the first three-dimensional gather 8 (the folded portion 7c of the gather-forming nonwoven fabric 7) is formed in a range of 80 to 30% and preferably 65 to 45% relative to the length W in the width direction of the member where the gather-forming nonwoven fabric 7 is arranged in plan view of the incontinence pad 1.

Moreover, in the length W1 along the width direction of the member of the folded portion 7*b* of the gather-forming nonwoven fabric 7, the width W2 in the pad width direction of the adhesive portion D (the width of the adhesive portion D) is preferable to be 40 to 80% of W1, while the length W3 along the width direction of the member of the projection 17 is preferable to be 60 to 20% of W1. The width W2 of the adhesive portion D is preferably formed to be almost same continuously from the end area Z1 to the middle area Z3.

The length L1, L2 in the pad longitudinal direction of the middle area Z3 is preferable to be 10 to 50 mm, and may be formed with a length different between the front side and the back side, as illustrated in the drawing, or may be a same length. The length L1, L2 of the middle area Z3 is preferably formed in a range shorter than the length L3, L4 in the pad longitudinal direction of the end area Z1 so as to prevent erection of the projection 17 at a position corresponding to a belly part or a buttock of a wearer. However, in order to securely maintain erection of the first three-dimensional gather 8 in the urinary-opening facing area Z2, the length L1, L2 of the middle area Z3 can be also formed in a range longer than the length L3, L4 of the end area Z1 depending on the entire length of the incontinence pad 1, such as the case in which the length of the incontinence pad 1 is short.

Second Embodiment

In the incontinence pad 1 according to the second embodiment, the first three-dimensional gather 8 is a double gather obtained by folding back the gather-forming nonwoven fabric 7 to the side at a position on the inner side of the absorbent body 4 and folding back it to the inner side at a side position of the absorbent body 4, as illustrated in FIG. 8.

To be more specific, in the end area Z1 and the middle area Z3, the gather-forming nonwoven fabric 7 adhered, at the adhesive portion C, on the side of the liquid permeable surface sheet 3 is folded in three by the first folded portion 20 folded to the side at an inner side portion and a second folded portion 21 folded to the inner side at a side portion, following the first folded portion 20. The gather-forming nonwoven fabric 7 has a first folded surface 22, a second folded surface 23, and a third folded surface 24 in the order from the lower layer side. The second folded surface 23 is adhered on the first folded surface 22 at the adhesive portion D formed at a position closer to the first folded portion 20, and the third folded surface 24 is adhered on the second folded surface 23 at an adhesive portion E formed at a position closer to the end side. Then, the area from a portion extending to the side rather than the adhesive portion D on the second folded surface 23 to the second folded portion 21 and then the adhesive portion E on the third folded surface 24, constitutes a projection 17' with an end of a portion on the outer side in the width direction than such adhesive portions as a free end.

The adhesive portion D and the adhesive portion E are preferably formed only in an area overlapping the absorbent body 4 in plan view.

In the urinary-opening facing area Z2 and the middle area Z3, the elastic stretching member 15 is arranged continuously at least in a region corresponding to an end portion of the projection 17', that is, the second folded portion 21 along the pad longitudinal direction, and the elastic stretching member 15 is arranged at the end portion of the third folded surface 24. Thus, in the urinary-opening facing area Z2, the first three-dimensional gather 8 erect on a skin side with a substantially Z-shaped cross section is formed, and in the middle area Z3, the projection 17' is erected on a skin side.

OTHER EMBODIMENTS (1) In the embodiment described above, the first three-dimensional gather 8 and the second three-dimensional gather 9 are formed using a single piece of gather-forming nonwoven fabric 7. However, they can be formed using different nonwoven fabric.

(2) In the embodiment described above, on the relatively outer side of the first three-dimensional gather 8, there is formed the second three-dimensional gather 9 erect on a skin side by nonwoven fabric arranged to be substantially continuous from the surface of the liquid impermeable back surface sheet 2. However, the incontinence pad may include only the first three-dimensional gather 8 without the second three-dimensional gather 9 formed.

The invention claimed is:

1. An absorbent article comprising:
an absorbent body interposed between a liquid permeable surface sheet and a back surface sheet; and
a pair of first three-dimensional single gathers erect on a skin side formed by only a single fold of a nonwoven fabric forming a folded portion constituted of an upper layer and a lower layer of the nonwoven fabric, each of the first three-dimensional single gathers being arranged at a respective side portion of the liquid permeable surface sheet along a longitudinal direction of the absorbent article, towards an outer side of the absorbent article in a width direction of the absorbent article at a position on an inner side of the absorbent body,
wherein a face of the lower layer faces the liquid permeable surface sheet and is adhered to a side edge portion of the liquid permeable surface sheet to constitute a joint portion with the single fold at an inner side of the joint portion, and the upper layer has a free edge extending in the longitudinal direction of the absorbent article, the folded nonwoven fabric having areas, in the longitudinal direction of the absorbent article, as follows:
an end area at both ends in the longitudinal direction of the absorbent article,
a urinary-opening facing area including a region corresponding to a urinary opening and in which the first three-dimensional gather is formed, and
a middle area between the end area and the urinary-opening facing area,
wherein, in the end area and the middle area, in addition to the lower layer of the folded nonwoven fabric adhering to the liquid permeable surface sheet, another portion of the nonwoven fabric, projects outside of the absorbent body and has a free longitudinal edge constituting a projection,
wherein, in the urinary-opening facing area and the middle area, an elastic stretching member is
arranged continuously or discontinuously at least in a region corresponding to the projection, along the longitudinal direction of the absorbent article and not arranged in the end areas on both ends in the longitudinal direction, and further wherein, in the urinary-opening facing area, the first three-dimensional gather is configured such that the entire folded portion is erected on the skin side, and the projection is erected on the skin side in the middle area.

2. The absorbent article according to claim 1, further comprising a second three-dimensional gather erect on a skin side by nonwoven fabric arranged to be substantially continuous from a surface of the back surface sheet, on a relatively outer side of the three-dimensional gather.

3. The absorbent article according to claim 1, further comprising a second gather having a second gather folded portion and wherein the projection is 20-60% of the length of the second gather folded portion in a width direction of the absorbent article.

* * * * *